United States Patent
Zhang

(10) Patent No.: US 10,932,783 B2
(45) Date of Patent: Mar. 2, 2021

(54) CIRCULAR STAPLER WITH AUDIBLE INDICATOR MECHANISM

(71) Applicant: Covidien LP, Mansfield, MA (US)

(72) Inventor: Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 284 days.

(21) Appl. No.: 15/771,677

(22) PCT Filed: Nov. 13, 2015

(86) PCT No.: PCT/CN2015/094557
§ 371 (c)(1),
(2) Date: Apr. 27, 2018

(87) PCT Pub. No.: WO2017/079970
PCT Pub. Date: May 18, 2017

(65) Prior Publication Data
US 2018/0296219 A1   Oct. 18, 2018

(51) Int. Cl.
*A61B 17/115*   (2006.01)
*A61B 17/00*   (2006.01)
*A61B 90/00*   (2016.01)

(52) U.S. Cl.
CPC .......... *A61B 17/1155* (2013.01); *A61B 90/00* (2016.02); *A61B 2017/00115* (2013.01);
(Continued)

(58) Field of Classification Search
CPC ........ A61B 17/1155; A61B 2090/0811; A61B 2017/00115; A61B 2017/00128;
(Continued)

(56) References Cited

U.S. PATENT DOCUMENTS 3,193,165 A   7/1965   Akhalaya et al.
3,388,847 A   6/1968   Kasulin et al.
(Continued)

FOREIGN PATENT DOCUMENTS

CA   908529 A   8/1972
CA   2805365 A1   8/2013
(Continued)

OTHER PUBLICATIONS

European search report dated Jul. 12, 2019, issued in EP Appln. No. 15908100.
(Continued)

*Primary Examiner* — Anna K Kinsaul
*Assistant Examiner* — Veronica Martin
(74) *Attorney, Agent, or Firm* — Carter, DeLuca & Farrell LLP

(57) ABSTRACT

A surgical stapling device includes a handle assembly that supports an audible indicator mechanism including a spring biased clicker. The spring biased clicker includes a pin that is received within a pin slot or cavity in the housing of a stationary handle of the handle assembly. The pin is movable through the cavity in response to actuation of the firing trigger assembly and unapproximation of the anvil assembly to guide movement of the clicker such that the clicker 1) provides an enhanced audible indication to a clinician that the firing stroke of a firing trigger has been completed, and 2) provides an enhanced indication to a clinician that the anvil assembly has been moved back to the unapproximated or spaced position after the firing stroke has been completed.

18 Claims, 9 Drawing Sheets

(52) U.S. Cl.
CPC .............. *A61B 2017/00128* (2013.01); *A61B 2017/00367* (2013.01); *A61B 2090/0811* (2016.02)

(58) Field of Classification Search
CPC .... A61B 2017/00367; A61B 5/150809; A61B 5/150816
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A * | 3/1996 | Brady .................. A61B 17/072 227/176.1 |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |

(56) References Cited

U.S. PATENT DOCUMENTS

| | | |
|---|---|---|
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |

(56) References Cited

U.S. PATENT DOCUMENTS

| | | | |
|---|---|---|---|
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 10,188,386 B2 * | 1/2019 | Measamer ......... A61B 17/1155 |
| 10,517,601 B2 * | 12/2019 | Murugesan ........ A61B 17/1155 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0085015 A1 * | 4/2006 | Whitfield ............... A61B 17/10 606/142 |
| 2006/0201989 A1 | 9/2006 | Ojeda |
| 2006/0235440 A1 * | 10/2006 | Huitema ............ A61B 17/1285 606/142 |
| 2007/0027473 A1 | 2/2007 | Vresh et al. |
| 2007/0029363 A1 | 2/2007 | Popov |
| 2007/0049948 A1 * | 3/2007 | Menn ................. A61B 17/1285 606/142 |
| 2007/0060952 A1 | 3/2007 | Roby et al. |
| 2007/0095877 A1 * | 5/2007 | Racenet ............... A61B 17/072 227/175.2 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 * | 3/2010 | Milliman ............. A61B 17/115 227/175.1 |
| 2010/0057106 A1 | 3/2010 | Sorrentino et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |

(56) References Cited

U.S. PATENT DOCUMENTS

| | | |
|---|---|---|
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1* | 7/2013 | Milliman ............ A61B 17/1155 227/175.1 |
| 2013/0175318 A1 | 7/2013 | Felder et al. |
| 2013/0175319 A1 | 7/2013 | Felder et al. |
| 2013/0175320 A1* | 7/2013 | Mandakolathur Vasudevan ......... A61B 17/1155 227/175.2 |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1* | 10/2013 | Ma .................. A61B 1/00087 227/176.1 |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2013/0325057 A1* | 12/2013 | Larson ............... A61B 18/1445 606/205 |
| 2014/0008413 A1 | 1/2014 | Williams |
| 2014/0012317 A1 | 1/2014 | Orban et al. |
| 2015/0005788 A1 | 1/2015 | Sniffin et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0189132 A1* | 7/2017 | Adams ................ A61B 90/08 |
| 2020/0046328 A1* | 2/2020 | Zammataro ........... A61B 17/00 |

FOREIGN PATENT DOCUMENTS

| | | |
|---|---|---|
| CN | 103462665 A | 12/2013 |
| CN | 203506807 U | 4/2014 |
| CN | 104334096 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2839786 A1 | 2/2015 |
| EP | 3108821 A2 | 12/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

OTHER PUBLICATIONS

European Search Report dated Oct. 18, 2019, issued in EP Appln. No. 15908100.

Chinese Office Action dated Jun. 3, 2020, issued in corresponding CN Appln. No. 201580084352, 11 pages.

\* cited by examiner

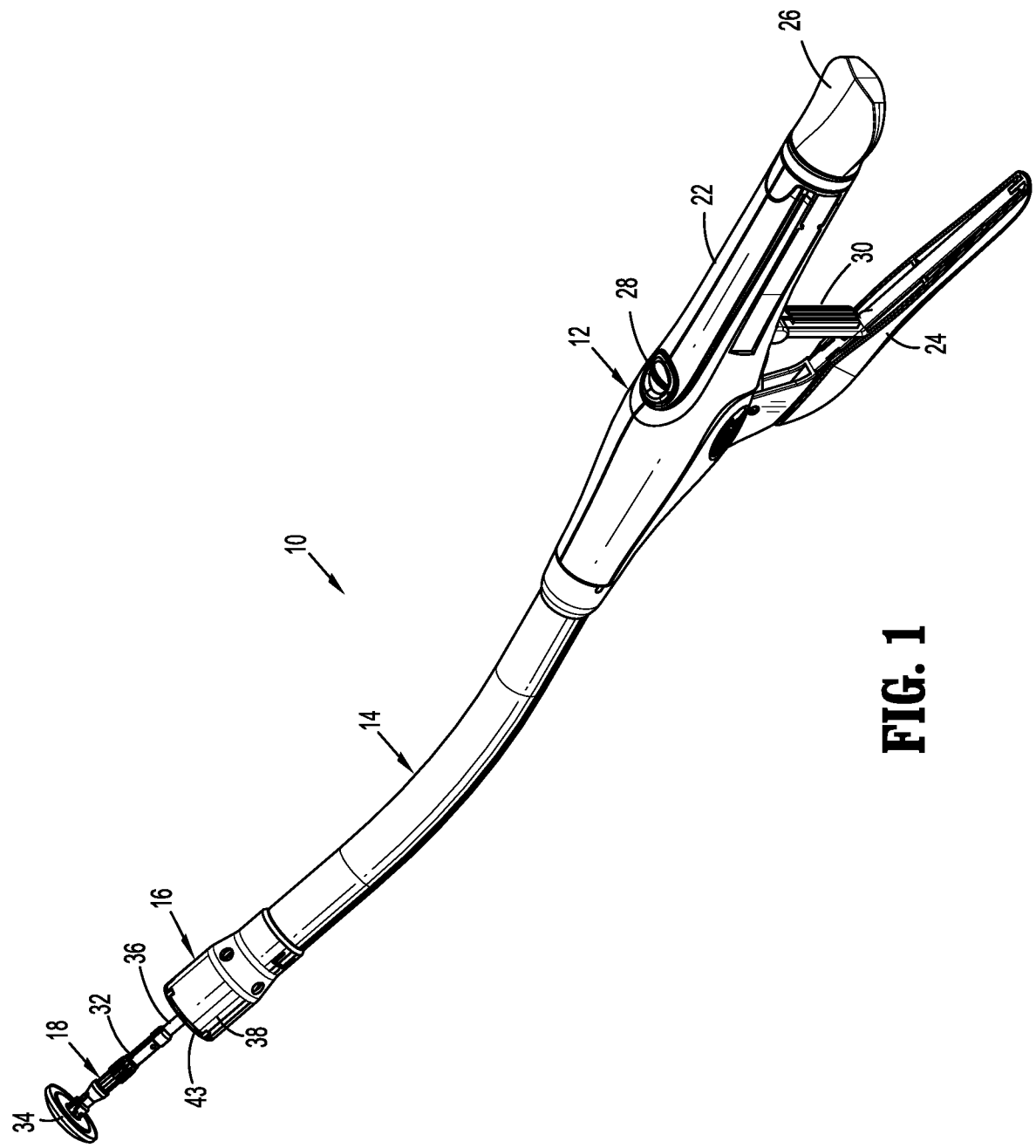

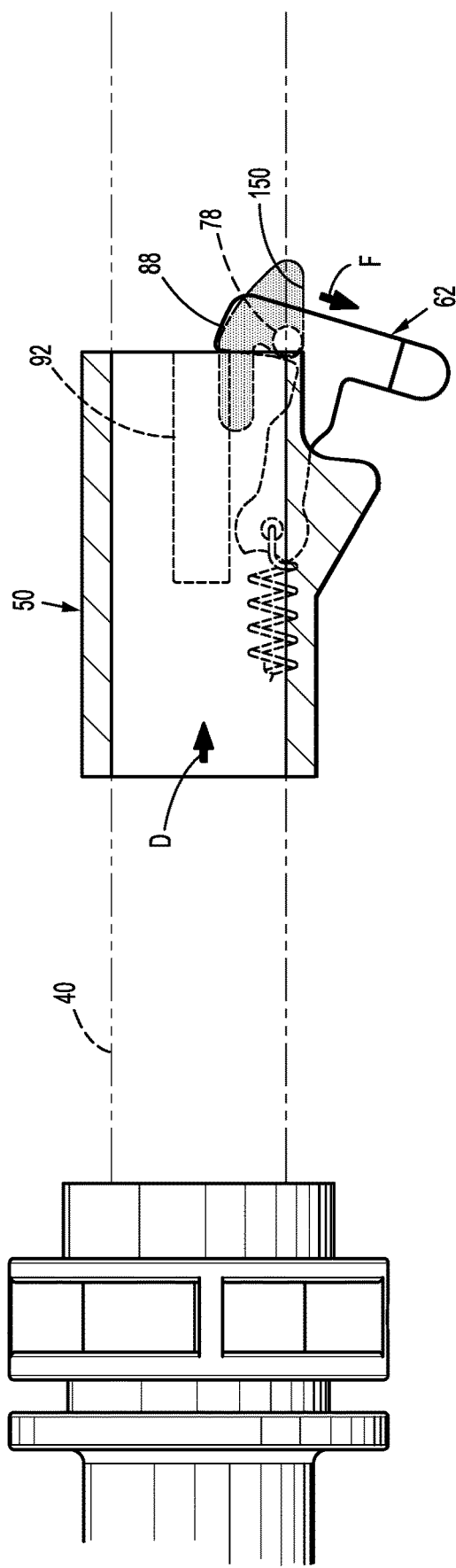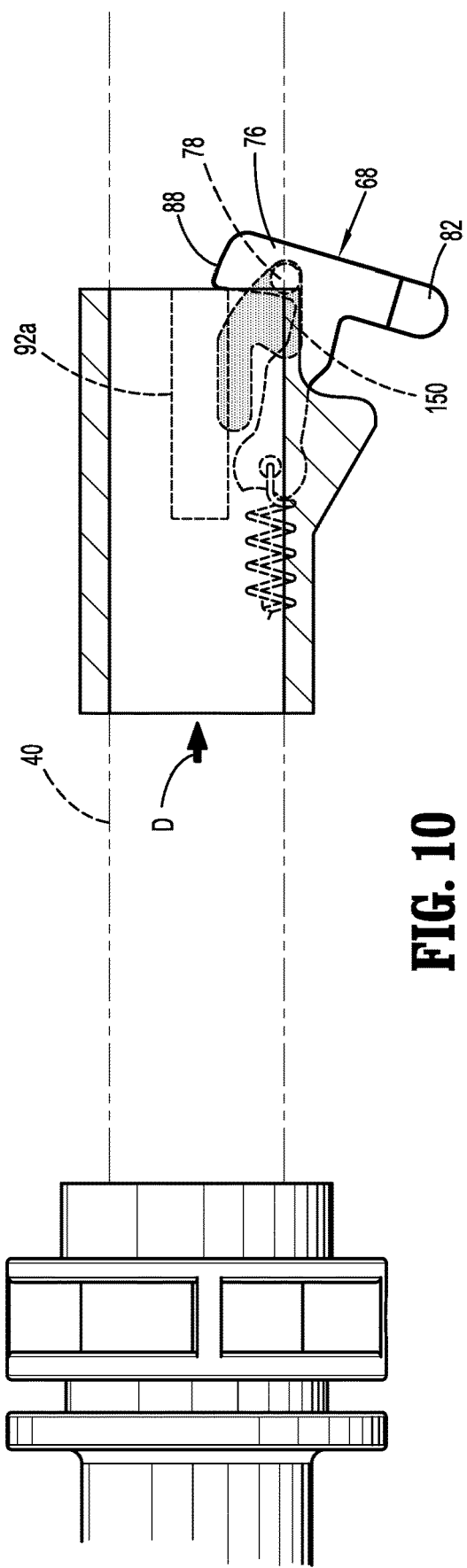
FIG. 9
FIG. 10

CIRCULAR STAPLER WITH AUDIBLE INDICATOR MECHANISM

CROSS-REFERENCE TO RELATED APPLICATIONS

This application is a U.S. National Stage Application filed under 35 U.S.C. § 371(a) which claims the benefit of and priority to International Patent Application Serial No. PCT/CN2015/094557, filed Nov. 13, 2015, the entire disclosure of which is incorporated by reference herein.

BACKGROUND

1. Technical Field

The present disclosure relates to surgical stapling devices, and more particularly, to circular stapling devices that include audible indicator mechanisms.

2. Background of Related Art

Anastomosis is the surgical joining of separate hollow organ sections. In known circular anastomosis procedures, two ends of organ sections are joined by means of a surgical stapling device that drives a circular array of staples through each organ section and simultaneously cores any tissue interior of the driven circular array of staples to free a tubular passage. Examples of such devices are described in U.S. Pat. Nos. 7,234,624, 6,945,444, 6,053,390, 5,568,579, 5,119,983, 4,646,745, 4,576,167, and 4,473,077, the content of each of which is incorporated herein by reference in its entirety.

Typically, a circular stapling device has an elongated shaft having a handle portion at a proximal end and a staple cartridge at a distal end. An anvil assembly including an anvil rod with an attached anvil head is mounted to the distal end of the device. The anvil is approximated to clamp tissue between a staple holding component of the staple cartridge and an anvil plate of the anvil assembly. In known circular stapling devices, the anvil assembly includes an anvil head that is movable from an operative position to a tilted position after the stapling device has been fired to minimize trauma to a patient upon removal of the anvil assembly from the patient.

Known circular stapling devices include indicator mechanisms that provide an audible and visual indication to a clinician that certain device operations have been completed. These operations include completion of a firing stroke and tilting of the anvil head. In known devices, the audible indication may not be loud enough to be clearly heard by the clinician.

It would be advantageous to provide a surgical stapling device including an audible indicator capable of clearly identifying to a clinician when specified device operations have been performed.

SUMMARY

The presently disclosed surgical stapling device includes a handle assembly that supports an audible indicator mechanism including a spring biased clicker. The spring biased clicker includes a pin that is received within a pin slot or cavity in the housing of a stationary handle of the handle assembly. The pin is movable through the cavity in response to actuation of the firing trigger assembly and unapproximation of the anvil assembly to guide movement of the clicker such that the clicker 1) provides an enhanced audible indication to a clinician that the firing stroke of a firing trigger has been completed, and 2) provides an enhanced indication to a clinician that the anvil assembly has been moved back to the unapproximated or spaced position after the firing stroke has been completed. In surgical stapling devices having a tiltable anvil head, an indication that that the anvil assembly has been moved back to the unapproximated or spaced position may be warranted when an anvil head of the anvil assembly of the surgical stapling device is spaced from the cartridge assembly a sufficient distance to allow the anvil head to move to a tilted, low profile position, respectively.

In one aspect of the present disclosure, a surgical stapling device includes a handle assembly having a stationary handle and a firing trigger assembly that is movable through an actuating stroke. A central body extends distally from the handle assembly and a cartridge assembly is supported on a distal end of the central body. The surgical stapling device also includes an anvil assembly and an approximation mechanism including a longitudinally movable drive screw. The drive screw is operatively connected to the anvil assembly such that longitudinal movement of the drive screw effects movement of the anvil assembly in relation to the cartridge assembly between spaced and approximated positions. An audible indicator mechanism includes a clicker and a biasing member positioned to urge the clicker proximally within the stationary handle. The clicker is positioned to engage the firing assembly as the firing assembly is moved through the actuating stroke to move the clicker from a first position towards a second position to increase tension within the biasing member. The clicker is adapted to move from the second position to a third position by the biasing member to provide an audible indication to a clinician that the firing trigger assembly has completed the actuating stroke.

In embodiments, the firing assembly includes a firing trigger and a firing link having a tab positioned to engage the clicker to move the clicker from the first position to the second position.

In some embodiments, the stationary handle defines a cutout and the clicker supports a pin that is received in the cutout, wherein the pin is movable through the cutout to guide movement of the clicker between the first, second and third positions.

In certain embodiments, the cutout defines an upper channel portion and a lower cavity portion and the pin is movable upwardly along a proximal wall of the lower cavity portion from the first position to the second position and movable proximally within upper channel portion from the second position to the third position.

In embodiments, the clicker includes a lower portion having a tab positioned to engage the tab on the firing link.

In some embodiments, the drive screw supports an abutment and the clicker includes an upper portion positioned to engage the abutment when the clicker is moved upwardly to the third position after the actuating stroke of the firing assembly.

In certain embodiments, the stationary handle includes a shelf defining a slot, and the upper portion of the clicker extends through the slot when the clicker is in the third position.

In embodiments, the abutment is movable along the shelf when the anvil assembly is moved in relation to the cartridge assembly from the approximated position back towards the spaced position to move the clicker from the third position back towards the second position.

In some embodiments, the abutment is configured to pivot the clicker as the anvil assembly is moved in relation to the cartridge assembly back towards the fully spaced position such that the abutment passes over the clicker to allow the clicker to snap back to the first position to provide a second audible indication that the anvil assembly has returned to the spaced position.

In another aspect of the present disclosure, a surgical stapling device includes a handle assembly including a stationary handle and a firing trigger assembly that is movable through an actuating stroke. A central body extends distally from the handle assembly and a cartridge assembly is supported on a distal end of the central body. The surgical stapling device also includes an anvil assembly and an approximation mechanism including a longitudinally movable drive screw. The drive screw is operatively connected to the anvil assembly such that longitudinal movement of the drive screw effects movement of the anvil assembly in relation to the cartridge assembly between the spaced and approximated positions. An audible indicator mechanism is provided in the handle assembly and includes a clicker and a biasing member, wherein the clicker is adapted to engage the firing assembly to provide an audible indication to a clinician that the firing stroke of a firing trigger has been completed, and adapted to engage the approximation mechanism to provide an audible indication to a clinician that the anvil assembly has moved back to the spaced position after the actuating stroke.

BRIEF DESCRIPTION OF THE DRAWINGS

Various embodiments of the presently disclosed surgical stapling device including an audible indicator mechanism are described herein below with reference to the drawings, wherein:

FIG. 1 is a perspective view of one embodiment of the presently disclosed surgical stapling device with an anvil assembly in an unapproximated or spaced position;

FIG. 8A is a side partial cross-sectional view of the handle assembly of the surgical stapling device shown in FIG. 1 with the stationary handle removed and the drive screw shown in phantom after actuation of the firing trigger assembly of the surgical stapling device as the drive screw is advanced into engagement with the clicker of the audible indicator mechanism;

FIG. 9 is a side partial cross-sectional view of the handle assembly of the surgical stapling device shown in FIG. 1 with the stationary handle removed and the drive screw shown in phantom after actuation of the firing trigger assembly of the surgical stapling device as the drive screw is advanced to move the clicker of the audible indicator mechanism distally and downwardly within a guide slot of the stationary housing;

FIG. 10 is a side partial cross-sectional view of the handle assembly of the surgical stapling device shown in FIG. 1 with the stationary handle removed and the drive screw shown in phantom after actuation of the firing trigger assembly of the surgical stapling device as the drive screw is advanced to move the clicker of the audible indicator mechanism to a distal end of the guide slot;

DETAILED DESCRIPTION OF EMBODIMENTS

Figures 1A, 1B:
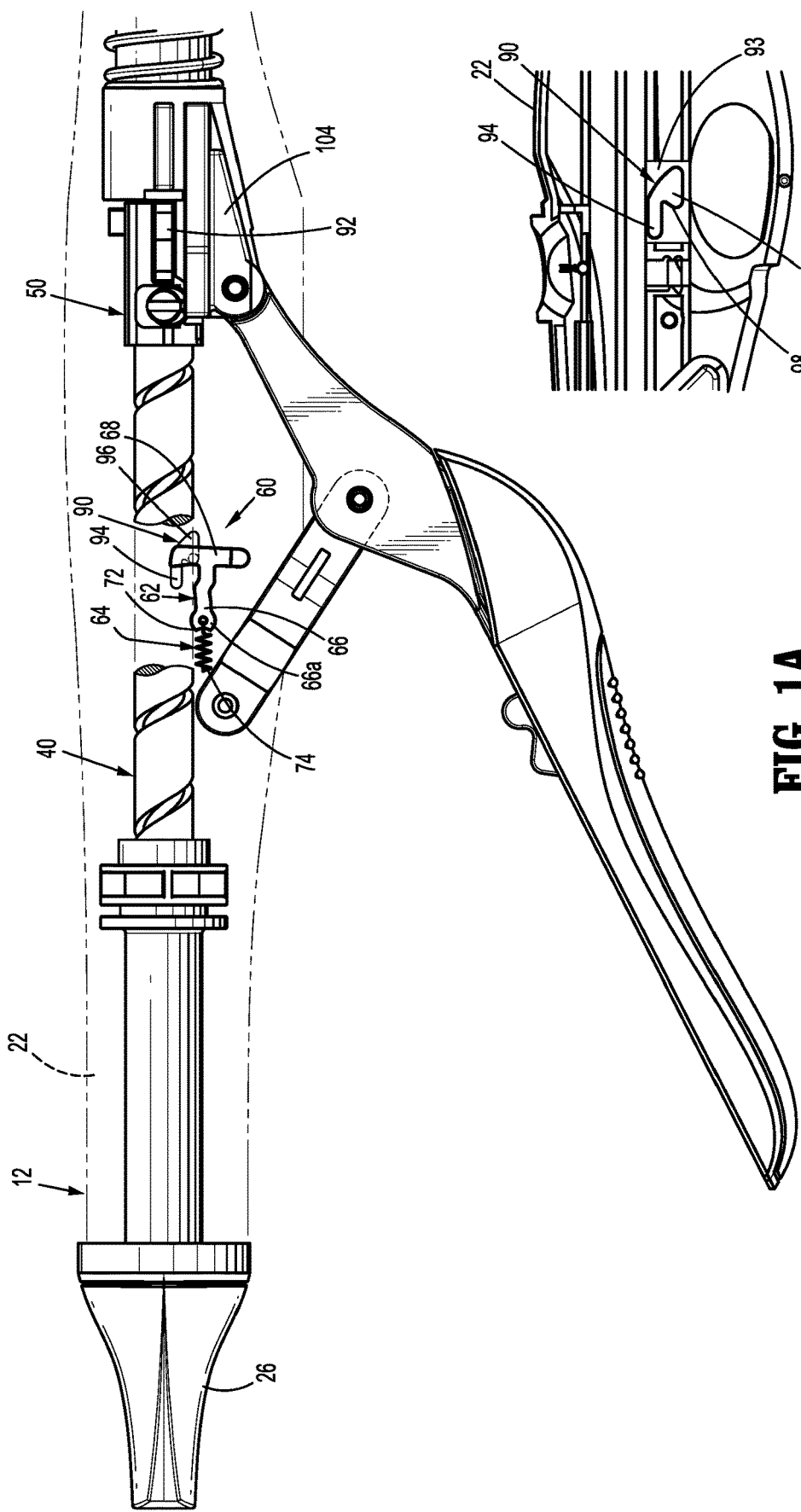
FIG. 1A is a side view of a handle assembly of the surgical stapling device shown in FIG. 1 with a stationary handle of the handle assembly shown in phantom and a drive screw positioned in a fully advanced position prior to firing of the surgical stapling device.
FIG. 1B is a side cutaway view of the inner wall of the stationary handle of the handle assembly of the surgical stapling device shown in FIG. 1.

The presently disclosed surgical stapling device will now be described in detail with reference to the drawings in which like reference numerals designate identical or corresponding elements in each of the several views. In this description, the term "proximal" is used generally to refer to the portion of the device that is closer to a clinician, while the term "distal" is used generally to refer to the portion of the device that is farther from the clinician. In addition, the term "endoscopic" is used generally to refer to procedures including endoscopic, laparoscopic, and arthroscopic performed through a small incision or a cannula inserted into a patient's body. Finally, the term clinician is used generally to refer to medical personnel including doctors, nurses, and support personnel.

The presently disclosed surgical stapling device includes a handle assembly that supports an audible indicator mechanism including a spring biased clicker. The spring biased clicker is positioned to engage a firing trigger assembly during firing of the surgical stapling device and a screw stop during unapproximation of the surgical stapling device and includes a pin that is received within a pin slot or cavity in the housing of a stationary handle of the handle assembly. The pin is movable through the cavity in response to actuation of the firing trigger assembly and unapproximation of the anvil assembly to 1) provide an enhanced audible indication to a clinician that the firing stroke of a firing trigger has been completed, and 2) provide an enhanced audible indication to a clinician that the anvil assembly has been moved back to the unapproximated or spaced position after the firing stroke has been completed. An indication that that the anvil assembly has been moved back to the unapproximated or spaced position may be warranted when an anvil head of the anvil assembly of the surgical stapling device is spaced from the cartridge assembly a sufficient distance to allow the anvil head to move to a tilted, low profile position.

FIG. 1 illustrates one embodiment of the presently disclosed surgical stapling device 10. Briefly, surgical stapling device 10 includes a handle assembly 12, a central body or elongated portion 14, a shell or cartridge assembly 16, and an anvil assembly 18. Although the central body portion 14 is shown to be slightly curved, it is to be understood that the central body portion 14 can be straight or have any degree of curvature suitable to perform a desired surgical procedure.

Except where otherwise noted, the components of stapler 10 are generally formed from thermoplastics including polycarbonates, and metals including stainless steel and aluminum. The particular material selected to form a particular component will depend upon the strength requirements of the particular component and upon whether the component is a reusable or disposable component. For example, the anvil assembly 18 may be formed from metal such as stainless steel, whereas portions of handle assembly 12 may be formed from thermoplastics such as a polycarbonate. In addition, the handle assembly 12 may be formed of an autoclavable material to allow for reuse whereas portions of the cartridge assembly may be formed of thermoplastics to allow for disposal. It is envisioned that other materials having the requisite strength requirements which are suitable for surgical use may be used to form the components of surgical stapler 10.

Figure 4:
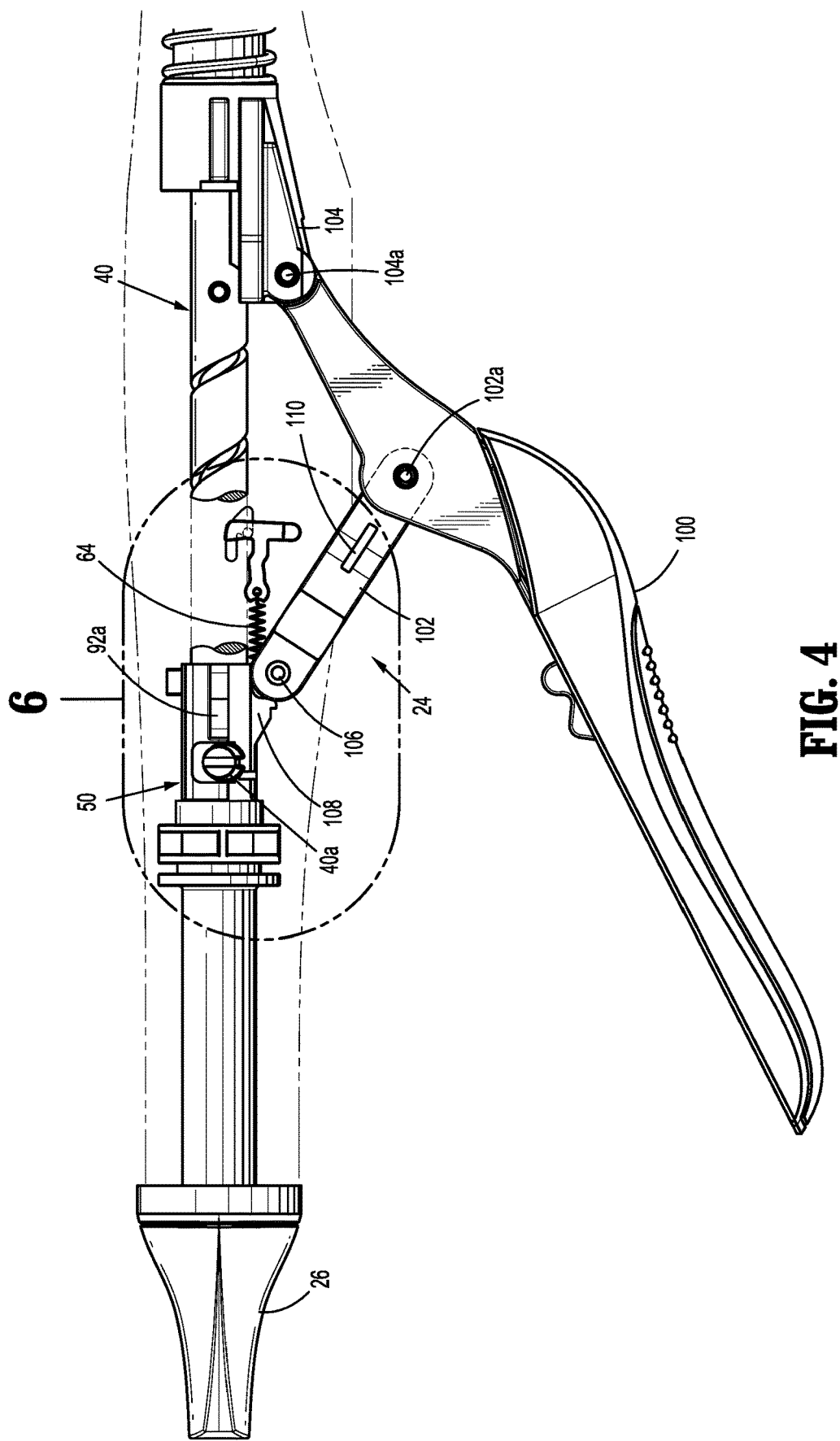
FIG. 4 is a side view of a handle assembly of the surgical stapling device shown in FIG. 1 with the stationary handle of the handle assembly shown in phantom and the drive screw in a fully retracted position prior to firing of the surgical stapling device.

Handle assembly 12 includes a stationary handle 22, a firing trigger assembly 24, an approximation knob 26, an indicator assembly 28, and a lockout mechanism 30. The approximation knob 26 functions to retract and advance a drive screw 40 (FIG. 4) to advance or retract the anvil assembly 18 in relation to the cartridge assembly 16 between spaced and approximated positions. The lockout mechanism 30 functions to prevent actuation of the firing trigger 24 until the anvil assembly 18 and the cartridge assembly 16 have been approximated into a firing zone, i.e., a position in which the tissue gap between the anvil and cartridge assemblies is reduced to an extent to allow for proper formation of staples. The firing trigger assembly 24 functions to actuate a pusher 104 (FIG. 1A) to eject staples from cartridge assembly 16 after the cartridge and anvil assemblies 16 and 18, respectively, have been approximated within the firing zone.

Each of the components of handle assembly 12 identified above are substantially as described in U.S. Pat. No. 7,303,106 ("'106 Patent") entitled "Surgical Stapling Device With Visual Indicator" which issued on Dec. 4, 2007. The '106 Patent is incorporated herein by reference in its entirety. Only those components of the handle assembly 12 that interact with the presently disclosed audible indicator mechanism will be described in further detail herein.

The anvil assembly 18 includes an anvil shaft or center rod 32 and an anvil head 34. In embodiments, the anvil head 34 is pivotally mounted to the distal end of anvil shaft 32 such that the anvil head 34 can move between an operative non-tilted position and a tilted position (not shown). Such an anvil assembly 18 is described in detail in the '106 Patent.

The cartridge assembly 16 is secured to the distal end of central body portion 14 of the surgical stapler 10 and includes a shell or housing 38. The housing 38 supports a pusher back (not shown), a knife (not shown), and a staple guide 43 (FIG. 1) that supports one or more annular arrays of staples. Details of the components of the cartridge assembly 16 are also provided in the '106 Patent.

Figure 5:
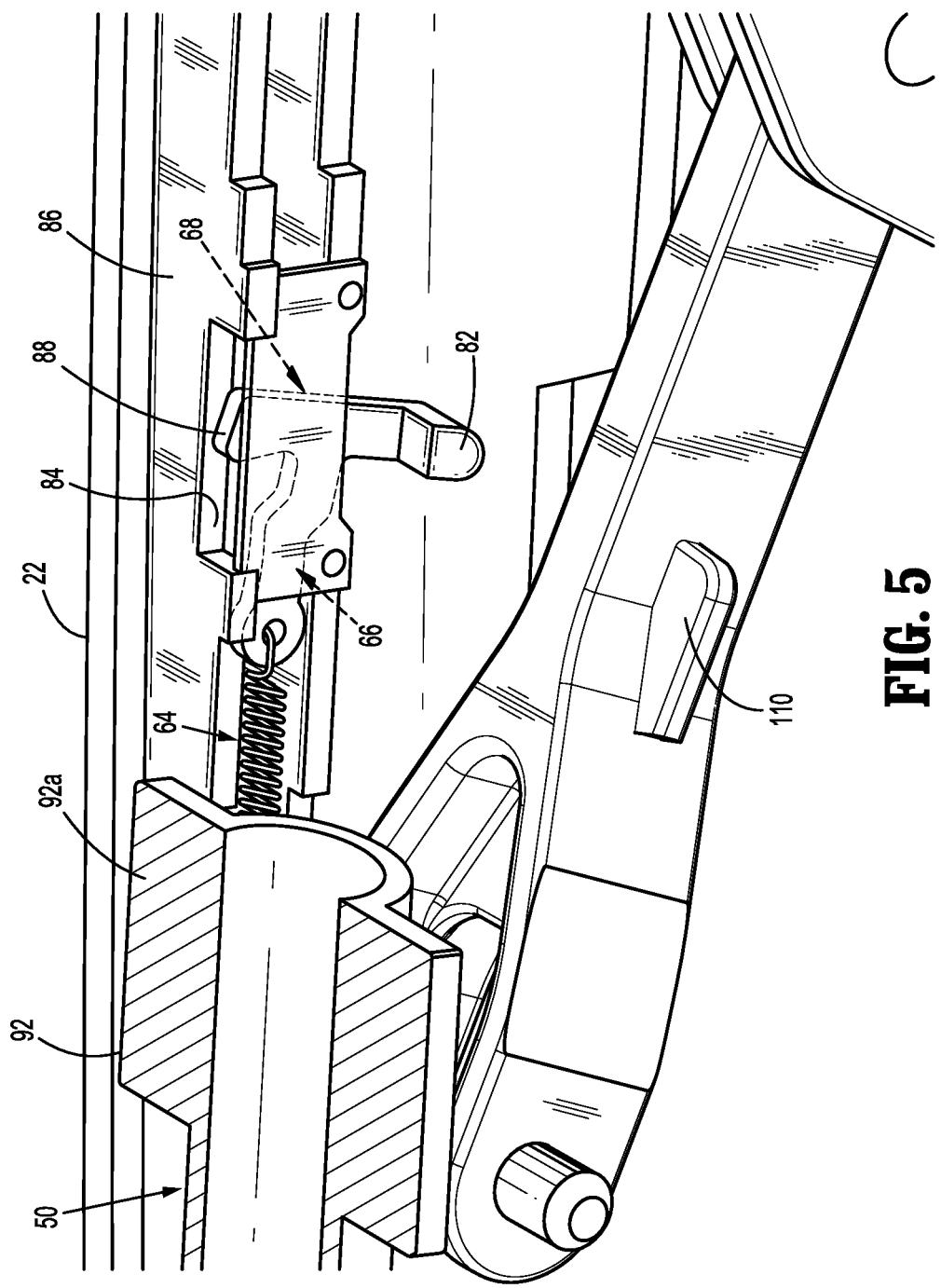
FIG. 5 is side perspective view of the handle assembly of the surgical stapling device shown in FIG. 1 with a portion of the stationary handle and the drive screw removed, and the screw stop shown in cross-section during actuation of the firing trigger assembly.

Referring also to FIG. 1A, the anvil assembly 18 (FIG. 1) is supported on the distal end of an approximation mechanism (not shown in its entirety) that includes the rotation knob 26, an anvil retainer 36 (FIG. 1) and the drive screw 40 (FIG. 1A). The rotation knob 26 is operably coupled to a proximal end of the drive screw 40 and the anvil retainer 36 is operably coupled to a distal end of the drive screw 40 such that actuation of the rotation knob 26 retracts and advances the drive screw 40 within the stationary handle 22 to move the anvil assembly 18 in relation to the cartridge assembly 16 between spaced and approximated positions. A screw stop 50 is fixedly supported on the drive screw 40 and includes an abutment 92 that moves along a shelf 86 (FIG. 5) defined within the stationary handle 22 as described in further detail below. Details of the approximation mechanism are provided in the '106 patent.

Figure 2:
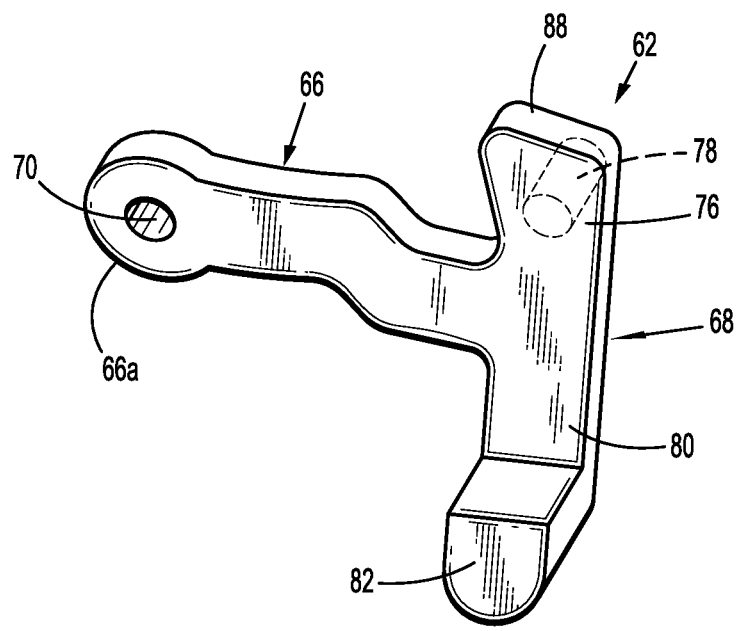
FIG. 2 is a side perspective view of a clicker of an audible indicator mechanism of the surgical stapling device shown in FIG. 1.
Figure 3:
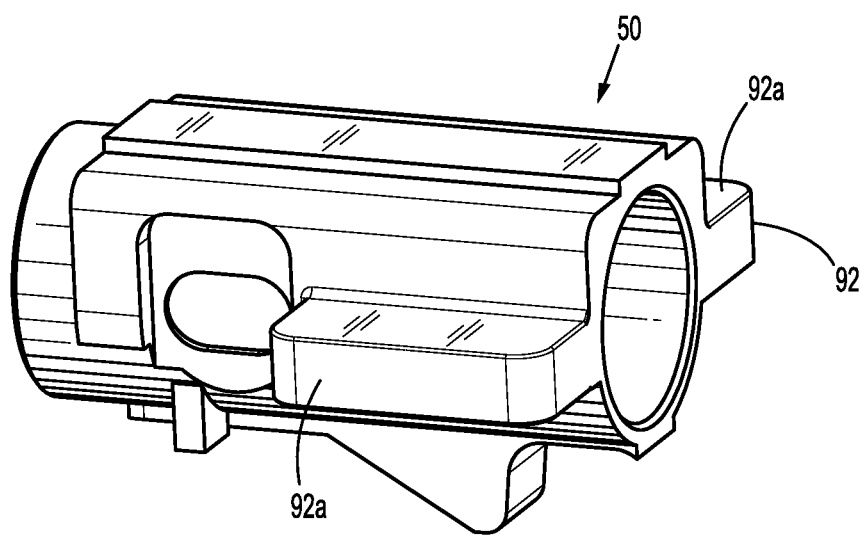
FIG. 3 is a side perspective view of the screw stop of the surgical stapling device shown in FIG. 1.

Referring also to FIGS. 1B and 2, the stationary handle 22 of the handle assembly 12 supports an audible indicator mechanism 60 that includes a clicker 62 (FIG. 2) and a biasing member 64, e.g., coil spring. In embodiments, the clicker 62 has a T-shape and includes a horizontal portion 66 and a vertical portion 68 as viewed in FIGS. 1A and 2. The proximal end 66a of the horizontal portion 66 of the clicker 62 defines an opening 70 (FIG. 2) that facilitates connection of the clicker 62 to a distal end 72 of the biasing member 64. A proximal end 74 of the biasing member 64 is fixedly secured to a wall of the stationary handle 22 such that the biasing member 64 is in tension and the clicker 62 is pulled proximally by the biasing member 64.

The vertical portion 68 of the clicker 62 includes an upper portion 76 supporting a pin 78 and a lower portion 80 supporting a tab 82. The upper portion 76 extends through a slot 84 (FIG. 5) defined in the shelf 86 of the stationary handle 22 and has a surface 88 that is angled downwardly in the distal direction as described in further detail below. The pin 78 is received within a cutout 90 formed in an inner sidewall 93 (FIG. 1B) of the stationary handle 22. The cutout 90 defines an upper channel portion 94 and a lower cavity portion 96 as viewed in FIG. 1A. The upper channel portion 94 extends proximally from a proximal wall 98 (FIG. 1B) of the lower cavity portion 96. In the pre-fired condition of the stapling device 10 with the clicker 62 in a first position, the pin 78 is positioned in the lower cavity portion 96 of the cutout 90 with the pin 78 urged against the proximal wall 98 of the lower cavity portion 96 by the biasing member 64. In embodiments, the proximal wall 98 is angled upwardly in the distal direction such that the biasing member 64 urges the pin 78 proximally along the proximal wall 98 into a lower corner of the cutout 90.

Figure 6:
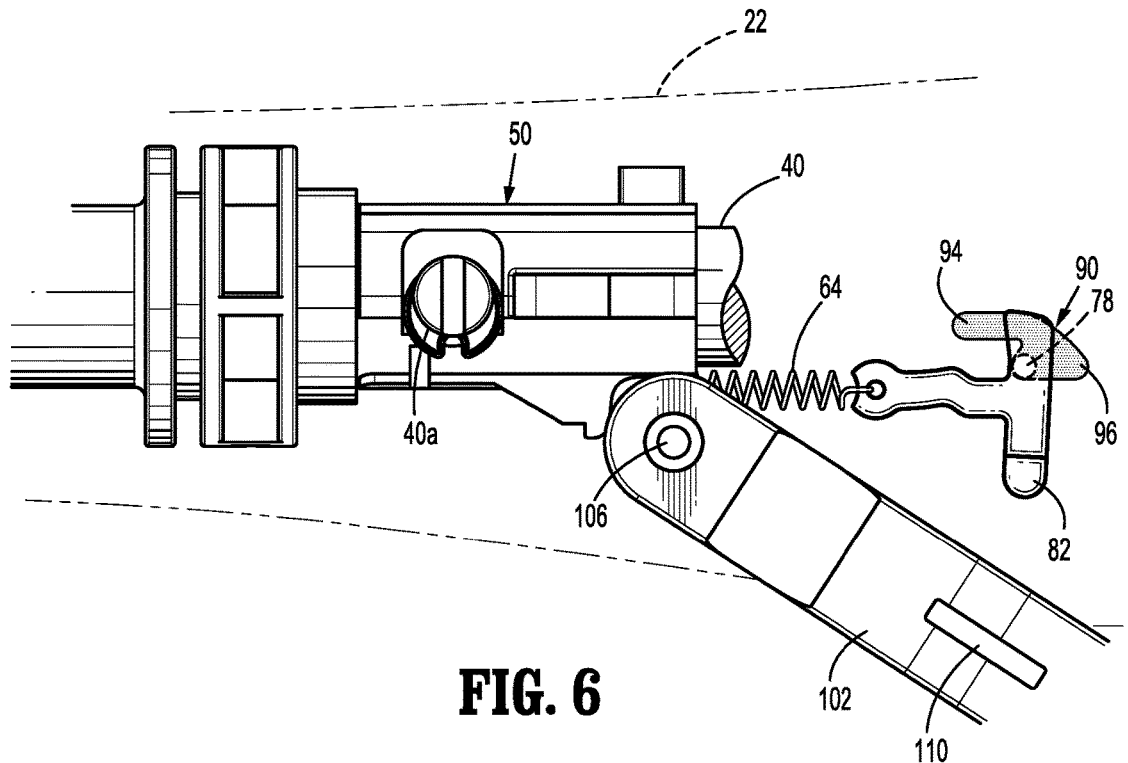
FIG. 6 is an enlarged view of the indicated area of detail shown in FIG. 4.

Referring to FIGS. 3-6, as discussed above, the screw stop 50 is fixedly secured to the drive screw 40 by a set screw 40a (FIG. 4) and includes an abutment 92 that is positioned to translate along the shelf 86 of the stationary handle 22. In one embodiment, the abutment 92 includes one of a pair of wings 92a (FIG. 5) that extend outwardly from the body of the screw stop 50. One of the wings 92a is positioned to pass over the slot 84 (FIG. 5) in the shelf 86 of the stationary handle 22 and into engagement with the angled surface 88 of the clicker 62. When the anvil assembly 18 is in an unapproximated or spaced position (FIG. 1) in relation to the cartridge assembly 16, the wing 92a of the screw stop 50 is positioned distally of the slot 84. When the drive screw 40 is retracted within the stationary handle 22 to move the anvil assembly 18 in relation to the cartridge assembly 16 towards the approximated position, the wing 92a of the screw stop 50 moves proximally over the slot 84 and the angled surface 88 of the clicker 62 such that the pin 78 of the clicker 62 remains positioned against the proximal wall 98 in the lower corner of cutout 90 (FIG. 6). Because the surface 88 of the clicker 62 is angled downwardly, a slight engagement between wing 92a and surface 88 of the clicker 62 during proximal movement of the screw stop 50 does not prevent proximal movement of the wing 92a over the clicker 62.

The firing assembly 24 includes a firing trigger 100 and a yoke or link 102. The distal end of the firing trigger 100 is pivotally coupled to a pusher 104 by a pin 104a and a central portion of the firing trigger 100 is pivotally coupled to a distal end of the link 102 by a pin 102a. A proximal end of the link 102 includes a pin 106 that is biased into engagement with an abutment 108 formed on the screw stop 50 when the drive screw 40 is in the retracted position (FIG. 4) such that when the firing trigger 100 is pivoted towards the stationary handle 22 through a firing stroke, the link 102 is pivoted from an angled orientation to an orientation aligned with a longitudinal axis of the stapling device 10 to drive the pusher 104 distally and eject staples from the cartridge assembly 16. This structure is described in detail in the '106 patent.

Figure 7:
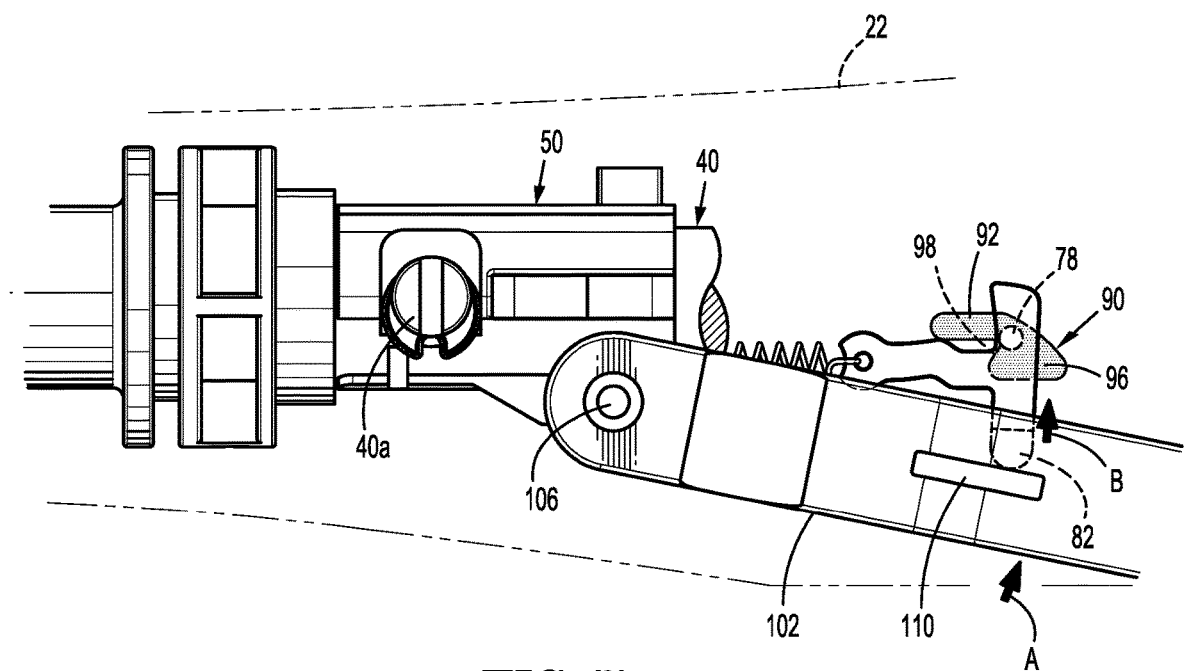
FIG. 7 is a side view of the handle assembly of the surgical stapling device shown in FIG. 1 with the stationary handle shown in phantom and the drive screw cutaway as a firing trigger assembly of the surgical stapling device is actuated and engages the clicker of the audible indicator mechanism.

Referring to FIG. 7, the link 102 includes a tab 110 that is positioned beneath the tab 82 of the clicker 62. When the firing trigger 100 is moved through the firing stroke and the link 102 is pivoted upwardly in the direction indicated by arrow "A" towards the clicker 62, the tab 110 of the link 102 of the firing assembly engages the tab 82 of the clicker 62 and lifts the clicker 62 from its first position upwardly in the direction indicated by arrow "B". As the clicker 62 is lifted upwardly towards a second position, the pin 78 that extends from a sidewall of the clicker 62 moves upwardly within the lower cavity portion 96 of the cutout 90 along the proximal wall 98 towards the upper channel portion 94 of the cutout 90. As discussed above, the proximal wall 98 is angled distally such that as the pin 78 moves upwardly along the wall 98, the tension in the biasing member 64 is increased.

Figure 8:
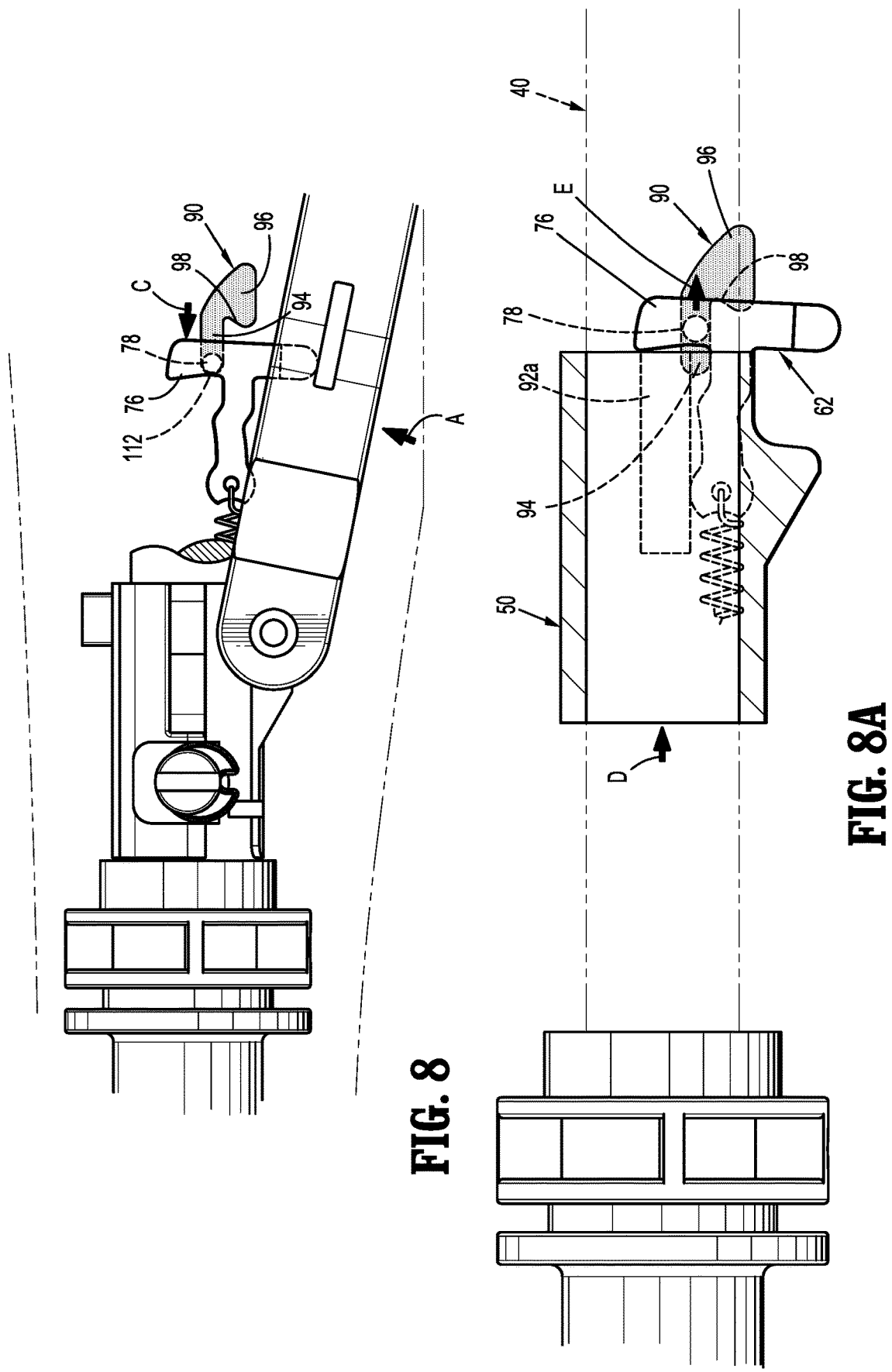
FIG. 8 is a side view of the handle assembly of the surgical stapling device shown in FIG. 1 with the stationary handle shown in phantom and the drive screw cutaway after actuation of the firing trigger assembly of the surgical stapling device.

Referring to FIG. 8, when the firing trigger 100 nears completion of the firing stroke, the clicker 62 moves from a second position in which the pin 78 is positioned adjacent an upper end of the proximal wall 98 towards a third position wherein the pin 78 passes off the upper end of the proximal wall 98 and moves to the proximal end of the upper channel portion 94 of the cutout 90. As described above, the upper channel portion 94 extends proximally from the lower cavity portion 96. As such, when the pin 78 moves into alignment with the upper channel portion 94 of the cutout 90, the biasing member 64, which is in tension, pulls the clicker 62 proximally within the stationary housing 22 in the direction indicated by arrow "C" to the third position such that the pin 78 moves proximally within the upper channel portion 94 of the cutout 90 and slams into an endwall 112 of the upper channel portion 94. Engagement between the pin 78 and the endwall 112 provides an enhanced audible indication to a clinician that the firing stroke is completed and that the firing trigger 100 can be released. With the pin 78 received in the upper channel portion 94 of the cutout 90, the clicker 62 is retained in a raised position such that the upper portion 76 of the clicker 62 extends further from the slot 84 to a position above the shelf 86.

Referring to FIG. 8A, after the stapling device 10 is fired, the anvil assembly 18 is moved towards the unapproximated position (FIG. 1) by actuating the rotation knob 26 (FIG. 1) to advance the drive screw 40 within the stationary handle 22 in the direction indicated by arrow "D". As the drive screw 40 is advanced within the stationary handle 22, the wing 92a of the screw stop 50 moves along the shelf 86 (FIG. 5) and engages the upper portion 76 of the clicker 62 to pull the clicker 62 distally with the screw stop 50, in the direction indicated by arrow "E", against the bias of the biasing member 64.

Referring to FIGS. 9 and 10, as the screw stop 50 continues to move distally within the stationary handle 22 in the direction indicated by arrow "D", the pin 78 moves out of the upper channel portion 94 and into the lower cavity portion 96 along the proximal wall 98 to tilt the clicker 62 in the direction indicated by arrow "F" to a lowered position in which the pin 78 rests on a bottom wall 150 of the lower cavity 96. In the lowered position, the upper end of the clicker 62 remains in engagement with the wing 92a of the screw stop 50 such that movement of the screw stop 50 distally continues to pull the clicker 62 distally until the pin 78 is pulled along the bottom wall 150 into engagement with the distal end of the lower cavity 96 of the cutout 90 (FIG. 10).

Figure 11:
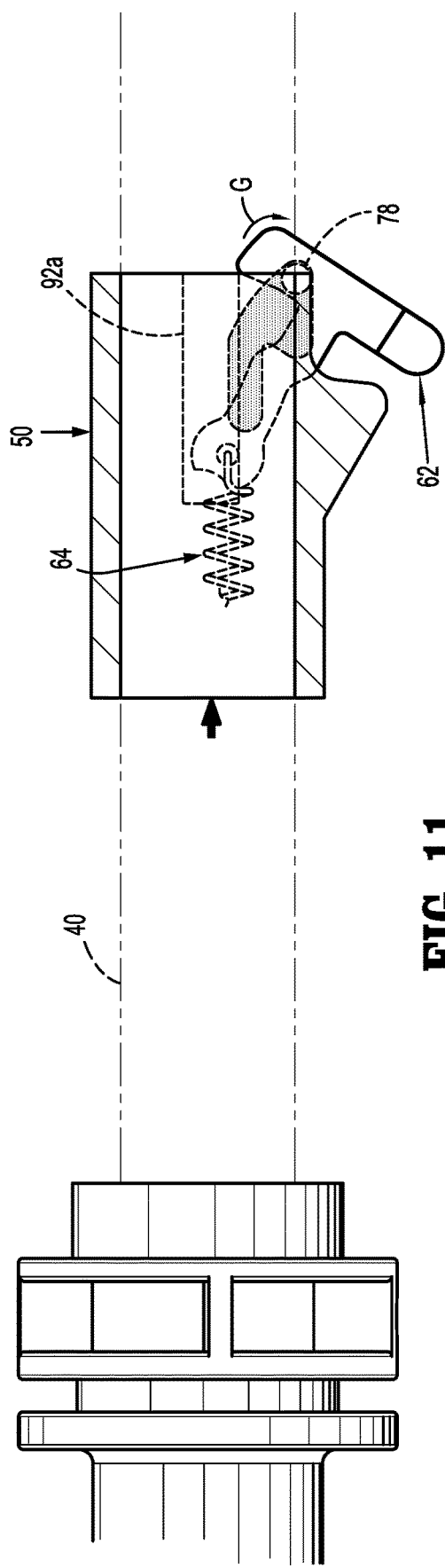
FIG. 11 is a side view of the handle assembly of the surgical stapling device shown in FIG. 1 with the stationary handle removed and the drive screw shown in phantom after actuation of the firing trigger assembly of the surgical stapling device as the screw stop of the drive screw begins to pass over the clicker of the audible indicator mechanism.
Figure 12:
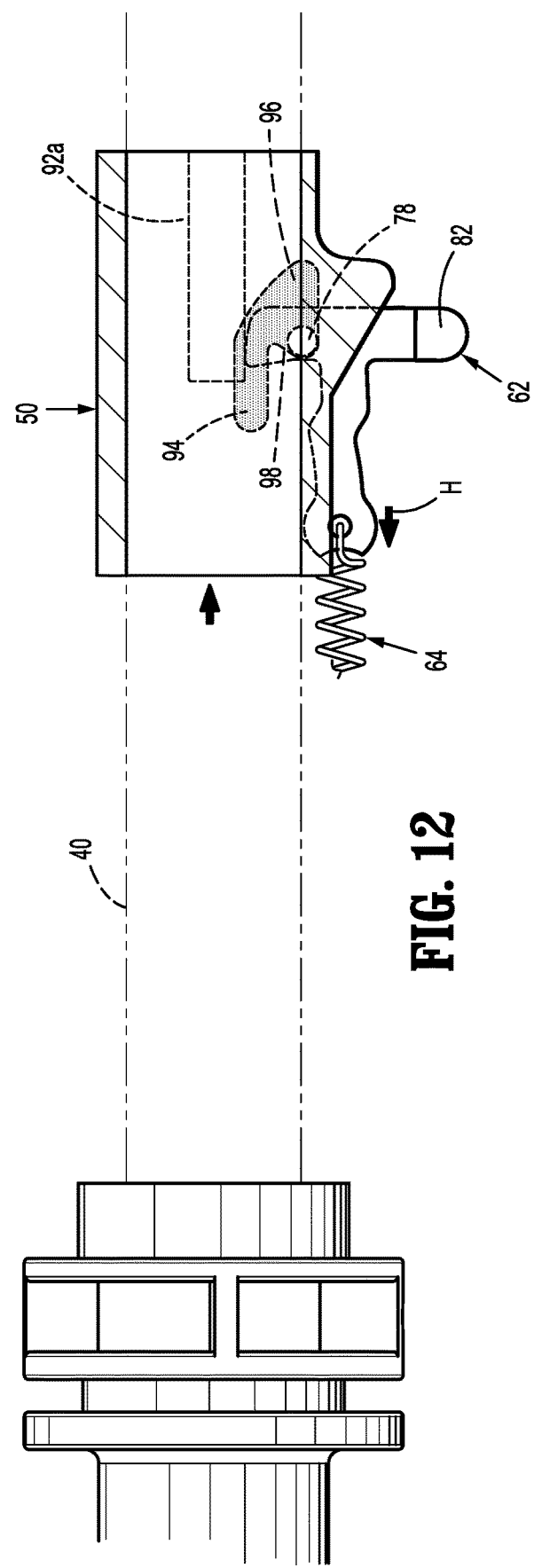
FIG. 12 is a side view of the handle assembly of the surgical stapling device shown in FIG. 1 with the stationary handle removed and the drive screw shown in phantom after actuation of the firing trigger of the surgical stapling device as the screw stop of the drive screw passes over the clicker of the audible indicator mechanism and the clicker snaps proximally to provide an audible indication that the anvil head of the anvil assembly has been approximated sufficiently to allow the anvil head to pivot.

Referring to FIGS. 11 and 12, when the pin 78 of the clicker 62 engages the distal wall of the lower cavity 96 of the cutout 90, further distal movement of the clicker 62 is prevented. As the screw stop 50 is moved further distally, engagement between the wing 92a and the upper end of the clicker 62 will cause the clicker 62 to pivot downwardly about the pin 78 in the direction indicated by arrow "G" in FIG. 11 to allow the wing 92a of the screw stop 50 to pass over the clicker 62. When the wing 92a passes over the clicker 62, the biasing member 64, which is in tension, pulls the clicker 62 proximally in the direction indicated by arrow "H" in FIG. 12 such that the pin 78 slams into the proximal wall 98 of the lower cavity portion 96 of the cutout 90. It is noted that in some embodiments, the wing 92a of the screw stop 50 is positioned to pass over the clicker 62 at the point of approximation when the anvil head 34 is spaced from the cartridge assembly 16 a sufficient distance to allow the anvil head 34 of the anvil assembly 18 to tilt to a low profile position. The '106 Patent discloses an anvil assembly including an anvil head that is movable from an operative position to a low profile tilted position.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
    a handle assembly including a stationary handle and a firing assembly, the firing trigger assembly being movable through an actuating stroke;
    a central body extending distally from the handle assembly;
    a cartridge assembly supported on a distal end of the central body;
    an anvil assembly;
    an approximation mechanism including a longitudinally movable drive screw, the drive screw being operatively connected to the anvil assembly such that longitudinal movement of the drive screw effects movement of the anvil assembly in relation to the cartridge assembly between spaced and approximated positions; and
    an audible indicator mechanism including a clicker and a biasing member positioned to urge the clicker proximally within the stationary handle, wherein the clicker is positioned to engage the firing assembly as the firing assembly is moved through the actuating stroke to move the clicker from a first position towards a second position to increase tension within the biasing member, the clicker being adapted to move from the second position to a third position by the biasing member to provide an audible indication to a clinician that the firing trigger assembly has completed the actuation stroke.

2. The surgical stapling device according to claim 1, wherein the firing assembly includes a firing trigger and a firing link, the firing link including a tab positioned to engage the clicker to move the clicker from the first position to the second position.

3. The surgical stapling device according to claim 2, wherein the stationary handle defines a cutout and the clicker supports a pin that is received in the cutout, the pin being movable through the cutout to guide movement of the clicker between the first, second and third positions.

4. The surgical stapling device according to claim 3, wherein the cutout defines an upper channel portion and a lower cavity portion, the pin being movable upwardly along a proximal wall of the lower cavity portion from the first position to the second position and movable proximally within upper channel portion from the second position to the third position.

5. The surgical stapling device according to claim 3, wherein the clicker includes a lower portion having a clicker tab, the clicker tab being positioned to engage the tab on the firing link.

6. The surgical stapling device according to claim 1, wherein the drive screw supports an abutment and the clicker includes an upper portion positioned to engage the abutment when the clicker is moved upwardly to the third position after the actuating stroke of the firing assembly.

7. The surgical stapling device according to claim 6, wherein the stationary handle includes a shelf defining a slot, an upper portion of the clicker extending through the slot when the clicker is in the third position.

8. The surgical stapling device according to claim 7, wherein the abutment is movable along the shelf when the anvil assembly is moved in relation to the cartridge assembly from the approximated position back towards the spaced position to move the clicker from the third position back towards the second position.

9. The surgical stapling device according to claim 8, wherein the abutment is configured to pivot the clicker as the anvil assembly is moved in relation to the cartridge assembly back towards the spaced position such that the abutment passes over the clicker to allow the clicker to snap back to the first position to provide a second audible indication that the anvil assembly has returned to the spaced position.

10. A surgical stapling device comprising:
    a handle assembly including a stationary handle and a firing assembly, the firing trigger assembly being movable through an actuating stroke;
    a central body extending distally from the handle assembly;
    a cartridge assembly supported on a distal end of the central body;
    an anvil assembly;
    an approximation mechanism including a longitudinally movable drive screw, the drive screw being operatively connected to the anvil assembly such that longitudinal movement of the drive screw effects movement of the anvil assembly in relation to the cartridge assembly between the spaced and approximated positions; and
    an audible indicator mechanism including a clicker and a biasing member, wherein the clicker is adapted to engage the firing assembly to provide a first audible indication to a clinician that the firing stroke of a firing trigger has been completed, and adapted to engage the approximation mechanism to provide a second audible indication to a clinician that the anvil assembly has moved back to the spaced position after the actuating stroke.

11. The surgical stapling device according to claim 10, wherein the firing assembly includes a firing trigger and a firing link, the firing link including a tab positioned to engage the clicker to move the clicker from the first position to the second position.

12. The surgical stapling device according to claim 11, wherein the stationary handle defines a cutout and the clicker supports a pin that is received in the cutout, the pin being movable through the cutout to guide movement of the clicker.

13. The surgical stapling device according to claim 12, wherein the cutout defines an upper channel portion and a lower cavity portion, the pin being movable from a first position upwardly along a proximal wall of the lower cavity portion to a second position adjacent an upper end of the proximal wall and movable from the second position proximally within upper channel portion to a third position.

14. The surgical stapling device according to claim 12, wherein the clicker includes a lower portion having a clicker tab, the clicker tab being positioned to engage the tab on the firing link.

15. The surgical stapling device according to claim 13, wherein the drive screw supports an abutment and the clicker includes an upper portion positioned to engage the abutment when the clicker is moved upwardly to the third position after the actuating stroke of the firing assembly.

16. The surgical stapling device according to claim 15, wherein the stationary handle includes a shelf defining a slot, the upper portion of the clicker extending through the slot when the clicker is in the third position.

17. The surgical stapling device according to claim 16, wherein the abutment is movable along the shelf when the anvil assembly is moved in relation to the cartridge assembly from the approximated position back towards the spaced position to move the clicker from the third position back towards the second position.

18. The surgical stapling device according to claim 17, wherein the abutment is configured to pivot the clicker as the anvil assembly is moved in relation to the cartridge assembly back towards the spaced position such that the abutment passes over the clicker to allow the clicker to snap back to the first position to provide the second audible indication that the anvil assembly has returned to the spaced position.

* * * * *